(12) United States Patent
Peters et al.

(10) Patent No.: US 7,479,277 B2
(45) Date of Patent: Jan. 20, 2009

(54) METHOD FOR REDUCING INTRAOCULAR PRESSURE USING INTEGRIN-LINKED KINASE INHIBITOR

(75) Inventors: Donna M. Peters, Middleton, WI (US); Jennifer A. Faralli née Peterson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/361,243

(22) Filed: Feb. 24, 2006

(65) Prior Publication Data

US 2006/0212007 A1 Sep. 21, 2006

Related U.S. Application Data

(60) Provisional application No. 60/655,782, filed on Feb. 24, 2005.

(51) Int. Cl.
*A61K 39/395* (2006.01)
*A61K 38/16* (2006.01)

(52) U.S. Cl. .......................... 424/146.1; 514/8; 514/44; 514/81

(58) Field of Classification Search .............. 424/142.1, 424/146.1; 514/172, 175, 8, 44, 81
See application file for complete search history.

(56) References Cited

U.S. PATENT DOCUMENTS

| | | | |
|---|---|---|---|
| 6,001,622 A | 12/1999 | Dedhar et al. | |
| 6,013,782 A | 1/2000 | Dedhar et al. | |
| 6,177,273 B1 | 1/2001 | Bennett et al. | |
| 6,214,813 B1 | 4/2001 | Zhang et al. | |
| 6,338,958 B1 | 1/2002 | Dedhar et al. | |
| 6,369,205 B1 | 4/2002 | Dedhar et al. | |
| 6,566,081 B1 | 5/2003 | Liao et al. | |
| 6,699,983 B1 | 3/2004 | Dedhar et al. | |

FOREIGN PATENT DOCUMENTS

WO    WO 03/045432 A1 *    6/2003

OTHER PUBLICATIONS

Clara Tan, Alice Mui, and Shoukat Dedhar, Integrin-linked Kinase regulates inducible Nitric Oxide synthase and Cyclooxygenase-2 Expression in an NF-kB-dependent Manner, Feb. 1, 2002, The Journal of Biological Chemistry vol. 277(5), 3109-3116.*

Shafiq A. Khan, Lilianne Ndjountche, Lauren Practchard, L.J. spicer and John S. Davis, Follicle-Stimulating Hormone amplifies Insulin-like Growth factor I-mediated activation of AKT/Protein Kinase B signalling in immature Rat Sertoli Cells, Endocrinology, 143(6), 2259-2267, 2002.*

Alpin A, et al., "Signal transduction and signal modulation by cell adhesion receptors: the role of integrins, cadherins, immunoglobulin-cell adhesion receptors: the role of integrins, cadherins, immunoglobulin-cell adhesion molecules, and selectins," Pharm, Rev. 50: 197-263 (1998).

Brakebusch C & Fässler R, "The Integrin-actin connection, an eternal love affair," EMBO J. 22:2324-2333 (2003).

Hu Y, et al., "Monkey organ-cultured anterior segments: technique and response to H-7," Exp. Eye Res. 82:1100-1108 (2006).

Johnson D & Tschumper R, "Human trabecular meshwork organ culture, A new method;" Invest. Ophthalmol. Vis. Sci. 28:945-953 (1987).

Khyrul W. "The integrin-linked kinase regulates cell morphology and motility in a Rho-associated kinase-dependent manner," J.B.C. 279:54131-54139 (2004).

Wu C & Dedhar S, "Integrin-linked kinase (ILK) and its interactors: a new paradigm for the coupling of extracellular matrix to actin cytoskeleton and signaling complexes," J. Cell. Biol. 155:505-510 (2001).

Dobreva I, et al., "Mapping the Integrin-Linked Kinase Interactome Using SILAC," J. Proteome Res. 7:1740-1749 (2008).

Weaver M, et al., "Expression of integrin-linked kinase in the murine lens is consistent with its role in epithelial-mesenchymal transition of lens epithelial cells in vitro," Mol. Vision 13:707-718 (2007).

* cited by examiner

*Primary Examiner*—Michael G. Hartley
*Assistant Examiner*—Jagadishwar R Samala
(74) *Attorney, Agent, or Firm*—Quarles & Brady LLP

(57) ABSTRACT

Methods for treating increased intraocular pressure by administering agents that interfere with activities of integrin-linked kinase. By interfering with the ability of integrin-linked kinase to couple integrin signaling to the actin cytoskeleton, aqueous humor outflow facility through the trabecular meshwork is increased and intraocular pressure is decreased.

2 Claims, No Drawings

METHOD FOR REDUCING INTRAOCULAR PRESSURE USING INTEGRIN-LINKED KINASE INHIBITOR

CROSS-REFERENCE TO RELATED APPLICATIONS

This application claims the benefit of U.S. Provisional Patent Application No. 60/655,782, filed Feb. 24, 2005, incorporated herein by reference as if set forth in its entirety.

STATEMENT REGARDING FEDERALLY SPONSORED RESEARCH OR DEVELOPMENT

This invention was made with United States government support awarded by the following agency: NIH-NEI Grant No. EY21515. The United States government has certain rights in this invention.

BACKGROUND OF THE INVENTION

The invention relates generally to a method for modulating intraocular pressure (IOP) in an eye of a human or non-human mammalian subject susceptible to or having elevated IOP, and more particularly to a method for modulating the IOP by treating the eye with an inhibitor of integrin-linked kinase.

When aqueous humor cannot drain normally from the anterior chamber of an eye, an animal can develop one of a family of ophthalmologic disorders. These disorders are characterized by above normal IOP and gradual neuropathy caused in some manner by increased pressure on the optic nerve. Pressure increase begins in the anterior chamber and extends to the other parts of the eye, including the posterior chamber. Under the force of the IOP, the posterior chamber compresses and destroys nerve fibers and blood vessels of the optic nerve. Such disorders can lead to gradual visual impairment and are collectively referred to as glaucoma. In a healthy mammalian eye, the aqueous humor is under resistance from the trabecular meshwork structures, generating a normal physiological IOP in a range from about 12-20 mmHg. The resistance directs and regulates outflow of aqueous humor from the eye.

Integrins are believed to help regulate IOP. They are found on virtually all human cells and transmit signals bi-directionally across a cell membrane. As cell surface receptors, integrins participate in a diverse array of biological functions including cellular development, cellular/tissue repair, angiogenesis, inflammation and hemostasis.

Integrin structure and function are known in the art. See Alpin A., et al., "Signal transduction and signal modulation by cell adhesion receptors: the role of integrins, cadherins, immunoglobulin-cell adhesion molecules, and selectins," Pharmacological Reviews 50: 197-263 (1998); and Brakebusch C. & Fässler R., "The integrin-actin connection, an eternal love affair," EMBO Journal 22:2324-2333 (2003), each of which is incorporated herein by reference as if set forth in its entirety. At least eighteen isoforms of the α-subunit and eight isoforms of the β-subunit combine to form more than twenty integrin heterodimers having α- and β-subunits. Human trabecular meshwork cells contain the following integrin subunits: $\alpha_1, \alpha_3, \alpha_4, \alpha_5, \alpha_6, \alpha_v, \beta_1, \beta_3, \beta_4$ and $\alpha_5$. Zhou L., et al., "Expression of integrin receptors in the human trabecular meshwork," Current Eye Research 19:395-402 (1999). Each integrin heterodimer has an extracellular domain, a transmembrane domain and a cytoplasmic tail.

The extracellular domain participates in cellular adhesion by binding to an Arg-Gly-Asp (RGD) amino acid sequence in a ligand. Known integrin ligands are ECM proteins including, but not limited to, vitronectin, fibronectin, type I and IV collagen and vascular cell adhesion molecule.

The cytoplasmic tail interacts with more than twenty intracellular constituents, linking the integrin to the actin cytoskeleton and forming focal adhesions, focal complexes and fibrillar adhesions. Signaling pathways also linked to the cytoplasmic tail of integrins are MAP kinase, FAK, JAK-STAT, JNK, inositol lipid pathway and Rho family of GTPases (including Rac and Cdc42).

Fibronectin interacts with cell surface receptors via two of its domains: (1) a central cell binding domain (CBD) and (2) a carboxy-terminal heparin-binding domain (Hep II). The CBD contains an RGD amino acid sequence that binds to an integrin; whereas, the Hep II domain contains three sequences that bind to cell surface receptors. Hep II has an amino acid sequence that binds to heparin-sulfate groups on a syndecan cell-surface receptor as well as an amino acid sequence (IDAPS) that binds to integrins. A third site called IIICS (type III) connecting sequence also contains a cell binding domain. This domain contains binding sites for integrins (LDV) as well as for cell surface proteoglycans.

The CBD and the Hep II domain together bring the integrin and the syndecan into proximity to mediate an intracellular signaling event that alters a cell's cytoskeleton. Cell signaling, mediated by the binding of fibronectin to integrins, involves integrin-linked kinase (ILK), a 59 kDa intracellular, cell-signaling enzyme. ILK interacts with the cytoplasmic tail of $\beta_1$- or $\beta_3$-subunits of integrin heterodimers. ILK also associates with other adaptor and signaling proteins such as PINCH, CH-ILKBP, affixin and paxillin, and with catalytic proteins such as ILKAP, PKB/Akt and PDK-1. See Wu C. & Dedhar S., "Integrin-linked kinase (ILK) and its interactors: a new paradigm for the coupling of extracellular matrix to actin cytoskeleton and signaling complexes," J. Cell. Biology 155: 505-510 (2001), incorporated herein by reference as if set forth in its entirety. See also, Khyrul W., "The integrin-linked kinase regulates cell morphology and motility in a Rho-associated kinase- dependent manner," J. B. C. 279:54131-54139 (2004), incorporated herein by reference as if set forth in its entirety.

ILK phosphorylates serine/threonine residues on other cell signaling molecules. ILK itself, however, must first be phosphorylated by phosphotidylinositol-3-kinase (PI3K) or by auto-phosphorylation. Conversely, ILK is negatively regulated by phosphatases, including PTEN and ILKAP. The cell-signaling molecules activated by ILK regulate cell survival, cell adhesion and ECM modification. ILK signaling also affects the regulation of cell migration, cell motility and contractility and is involved in suppressing apoptosis and in advancing the cell cycle.

Integrins, fibronectin and ILK interact to form focal adhesions, which are macromolecular complexes found where cells adhere to the extracellular matrix. Focal adhesions are linked to actin stress fibers and serve as signaling complexes for triggering intracellular cascades. Cell-to-ECM interactions with integrins, fibronectin and ILK are implicated in a variety of pathophysiological conditions, including glaucoma.

Glaucoma can be classified into two broad classes—open-angle and closed-angle glaucoma, each of which is subclassified into primary and secondary forms. In primary open-angle glaucoma (also known as POAG), the trabecular meshwork appears to not function properly. Aqueous humor outflow from the eye is restricted. Consequently, the aqueous humor builds up in the anterior chamber, increasing IOP because it cannot flow through the trabecular meshwork. The cause of this reduced outflow is not known. In secondary open-angle glaucoma, intraocular inflammation or the use of certain treatments such as steroids can increase IOP.

Current treatments for glaucoma include pharmacological and surgical therapies, either alone or in combination. All treatments can have significant side effects. Pharmacological agents, most commonly administered as eye drops, can be used alone or in combination to decrease aqueous humor production or to improve aqueous humor outflow from the eye. β-adrenergic blockers such as timolol, levobunolol and betaxolol decrease aqueous humor production. Side effects of β-adrenergic blockers can include cardiac failure, heart block and bronchospasm. Cholinergic agonists such as pilocarpine, carbachol, and phospholine iodide improve outflow facility from the trabecular meshwork. Side effects of cholinergic agonists can include miosis, brow ache and decreased vision. Carbonic anhydrase inhibitors such as acetazolamide, dorzolamide and brinzolamide decrease aqueous humor production. Side effects of carbonic anhydrase inhibitors can include gastrointestinal upset, malaise, renal stones and aplastic anemia. Non-selective α-agonists such as epinephrine and dipivefrin decrease aqueous humor production and increase trabecular outflow facility. Side effects of non-selective α-agonists can include pupil dilation, macular edema and tachycardia. Selective α-agonists such as apraclonidine and brimonidine decrease aqueous humor production and increase outflow through the uveoscleral pathway (an alternative, but smaller, fluid exit pathway to the trabecular meshwork). Side effects of selective α-agonists can include contact allergy and hypotension. Prostaglandin agonists such as latanoprost, travoprost and bimatoprost improve uveoscleral outflow. Side effects of prostaglandins can include iris color change, lash growth and trichiasis. Hyperosmotics such as glycerin (po) and mannitol (iv) establish a concentration gradient that draws excess aqueous humor from the eye. Side effects of using hyperosmotics can include diuresis, cardiovascular overload, renal insufficiency, and stroke, so their use is limited to emergency situations.

When pharmacological agents are unsuccessful in open-angle glaucoma or when a subject presents with closed-angle glaucoma, invasive surgery is indicated. In argon laser trabeculoplasty (ALT), a laser beam is directed at the trabecular meshwork that increases aqueous humor drainage through a mechanism that is not well understood. In laser cyclophotocoagulation, thermal energy applied to the ciliary body destroys the tissue, thereby reducing aqueous humor production. Trabeculectomy establishes a flow route that bypasses the trabecular meshwork so that aqueous humor drains from the anterior chamber just beneath the conjunctiva, the outermost covering of the eye, on the surface of the eye where it is gradually absorbed by blood vessels or diffuses through the conjunctiva. Iridotomy, generally used for closed-angle glaucoma, employs a laser to make an incision in a peripheral area of the iris of the eye to establish a direct aqueous humor flow route between the anterior chamber and the posterior chamber. Iridectomy is similar to iridotomy, but does not employ a laser. In iridotomy, a small section of peripheral iris is surgically excised.

Glaucoma is an increasingly important public health concern, especially in view of the aging of the population. Present treatments do not always adequately control glaucoma, especially steroid-induced glaucoma. Thus, there is a strong need to develop additional methods to prevent and treat the various forms of glaucoma.

SUMMARY OF THE INVENTION

The present invention relates to the observation that integrin-linked kinase (ILK) regulates actin cytoskeletal organization in cultured human trabecular meshwork cells, suggesting that the activities of these enzymes can be exploited to control cell contacts and contractility to thereby regulate intraocular pressure (IOP). In particular, it is herein disclosed that administration of an ILK inhibitor or an agent that interferes with ILK signaling to trabecular meshwork cells can disrupt actin cytoskeletal organization in the cells. Consequently, the contractile properties of the cells change and, in so changing, facilitate aqueous humor outflow from the trabecular meshwork, thereby reducing IOP.

In a first aspect, the present invention is a method for reducing IOP in an eye of a human or non-human mammalian animal subject susceptible to or having IOP elevated relative to a normal physiological IOP, by inhibiting ILK. The method includes the step of treating the eye with an amount of an ILK inhibitor sufficient to reduce the elevated IOP, thereby increasing aqueous humor outflow. The ILK inhibitor can be administered directly to the eye or provided indirectly via another route.

In some embodiments, the elevated IOP is caused by glaucoma that can be open angle glaucoma.

In some embodiments, the trabecular meshwork of the eye is treated with the ILK inhibitor.

In some embodiments, the ILK inhibitor is QLT0267, KP392 or KPSD1. In a preferred embodiment, the ILK inhibitor is QLT0267.

In some embodiments, the method includes co-administering with the ILK inhibitor an amount of a PI3K inhibitor sufficient to further reduce the IOP.

In some embodiments, the PI3K inhibitor is LY29400.

In some embodiments, the method also includes the step of quantifying the reduction in IOP resulting from the provision of the ILK inhibitor and optionally the PI3K inhibitor in combination with the ILK inhibitor. The quantifying step can include the steps of measuring aqueous humor outflow from the eye before and after the treating step.

In another aspect, the present invention is a method for reducing IOP in an eye of a human or non-human mammalian animal subject susceptible to or having IOP elevated relative to a normal physiological IOP, by interrupting ILK signaling. The method includes the step of treating the eye with an agent that interrupts ILK signaling in an amount sufficient to reduce the elevated IOP, thereby increasing aqueous humor outflow. The agent can be administered directly to the eye or provided indirectly via another route.

In some embodiments, the elevated IOP is caused by glaucoma that can be open angle glaucoma.

In some embodiments, the trabecular meshwork of the eye is treated with the agent.

In some embodiments, the agent is a PI3K inhibitor. In preferred embodiments, the PI3K inhibitor is LY29400.

In some embodiments, the method also includes the step of quantifying the reduction in IOP resulting from the provision of the agent and optionally the agent in combination with the ILK inhibitor. The quantifying step can include the steps of measuring aqueous humor outflow from the eye before and after the treating step.

One object of the present invention is to provide effective and non-invasive methods for increasing outflow from the trabecular meshwork and for reducing IOP.

A feature of the present invention is that ILK inhibition interrupts normal transduction of a signal cascade required to organize the actin cytoskeleton. The invention exploits this interruption to alter the shape and properties of trabecular meshwork cells such that outflow from the trabecular meshwork is enhanced.

An advantage of the present invention is that the treating step is non-invasive.

These and other objects, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

Not applicable.

DETAILED DESCRIPTION OF THE INVENTION

The present invention relates to modulating intraocular pressure (IOP) in an eye of a human or non-human mammalian subject having IOP that is elevated relative to a normal physiological IOP. The invention also relates to treating at least one eye of a human or non-human mammalian subject susceptible to experiencing an increase in IOP to prevent an increase in pressure to an abnormally high level.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As used herein, a sufficient amount is defined as an amount of an agent that yields IOP no higher than about 110% of normal physiological IOP. Suitable amounts can vary with the extent to which the IOP is elevated and with the efficiency of the agent(s). Suitable amounts can readily be determined experimentally in conventional eye organ culture systems for subsequent use in vivo in animals for which the eye organ culture systems are accepted pre-clinical models. The working examples provide guidance to the skilled artisan as to suitable amounts of the exemplified agents. Amounts higher or lower than the sufficient amounts used are also considered suitable. For example, amounts that are plus or minus any of 5%, 10%, 15%, 20% or 25% of an amount shown to be effective are also considered to be sufficient amounts.

Suitable mammalian subjects can include, but are not limited to, a primate, including a human, a rodent, a canine, a feline, a rabbit and the like.

Inhibitors of ILK are disclosed in various US patents, including U.S. Pat. Nos. 6,699,983; 6,566,081; 6,369,205; 6,338,958; 6,214,813; 6,177,273; 6,013,782 and 6,001,622, each incorporated herein by reference as if set forth in its entirety. These patents describe various structures having a shared common attribute of ILK inhibition.

Preferred routes of delivery of the ILK inhibitor and the agent that interrupts ILK signaling are topical or intravenous. The skilled artisan will appreciate the desirability of non-invasive administration of the antagonist. Accordingly, eye drops are a suitable delivery vehicle.

The invention will be more fully understood upon consideration of the following Examples.

EXAMPLES

Working Example: This example demonstrates that ILK inhibitor reduces the ability of cultured human trabecular meshwork cells to spread (i.e., to form polygonal flattened cells exhibiting cortical actin structures indicative of an assembled actin network) and a greater percentage of the cells are rounded and lack an organized actin network. In vivo, trabecular meshwork cells having a disrupted actin network, characterized by little actin structure, facilitate aqueous humor outflow. Accordingly, administering ILK inhibitor to the trabecular meshwork is useful for reversing the reduced outflow of aqueous humor associated with increased IOP and glaucoma.

A cultured human trabecular meshwork (HTM) diploid cell strain obtained from trabecular meshwork explants was serum-starved for twenty-four hours and then plated on 12 mm round glass coverslips (Bellco Glass, Inc.; Vineland, N.J.) coated with $III_{7-10}$ domains of fibronectin (RGD cell-binding domain; 236 nM) for three hours at 37° C., 95% humidity, 5% $CO_2$, ambient air. The cells were exposed to either DMSO (control) or an ILK inhibitor with or without 472 nM of the Hep II domain. Following incubation, cells were fixed for immunofluorescence microscopy by methods known to a skilled artisan.

HTM cells were examined by immunofluorescence microscopy using anti-vinculin (1:3000; Sigma-Aldrich; St. Louis, Mo.), anti-ILK (1:1000; Upstate Group, LLC; Charlottesville, Va.), anti-talin (1:1000; Chemicon; Temecula, Calif.), anti-paxillin (1:1000; BD Biosciences; San Jose, Calif.) or anti-FAK (1:1000; BD Biosciences) antibodies to reveal actin stress fibers and focal adhesions. The secondary antibody was Alexa 546-conjugated goat anti-mouse antibody (4 µg/ml; Molecular Probes; Eugene, Oreg.) and Alexa 488-conjugated phalloidin (0.67 units/ml; Molecular Probes). Cell images were acquired with a Zeiss AxioCam HRm camera mounted on a Zeiss Axiophan 2 Imaging fluorescence microscope together with AxioVision v.3.1 software. The percentage of spread cells was determined by counting polygonal cells containing stress fibers (spread cells) versus rounded cells lacking stress fibers (non-spread cells) from eight to twelve fields.

Of the control cells, 86.5% were spread cells. However, HTM cells exposed to KP392 (Quadra Logic Technologies, Inc.; Vancouver, British Columbia, Canada), at 100 µM for three hours reduced the percentage of spread cells to 36% ($p<0.027$). Likewise, the percentage of spread HTM cells was reduced to 14% after exposure to 20 µM QLT0267 (Quadra Logic Technologies, Inc), a KP392 derivative having enhanced cell permeability, for three hours. QLT0267 is more effective at lower concentrations than KP392 at preventing cell spreading.

In addition, cells exposed to either ILK inhibitor showed fewer focal adhesions than control cells. Furthermore, ILK inhibition decreased FAK phosphorylation and disrupted localization of talin, FAK, paxillin and ILK to focal adhesions.

When the HTM cells were exposed to both KP392 (100 µM) and a soluble Hep II domain of fibronectin (472 nM; type III 12-14 repeats), the effect of the inhibitor was reversed—73% of the cells were spread cells. Similarly, when the HTM cells were exposed to both QLT0267 (20 µM) and the soluble Hep II domain of fibronectin (472 nM), the effect of the inhibitor was reversed—50% of the cells were spread cells.

However, this effect was itself reversed by including with these cells a PI3K inhibitor, LY29400 (Calbiochem/EMD Biosciences; San Diego, Calif.; 25 µM)—only 28% of the cells were spread cells (p<0.008).

When administered alone, LY29400 decreased HTM cell spreading to 35% when compared to control cells (p<0.2). Interestingly, when KP392 and LY29400 were administered together, HTM cell spreading was reduced to just 14% when compared to control cells (p<0.001).

Prophetic example: A matched pair of anterior chambers obtained from human or monkey cadavers are prepared and mounted according to the procedure disclosed in Johnson D. & Tschumper R., "Human trabecular meshwork organ culture. A new method," Invest. Ophthalmol. Vis. Sci. 28:945-953 (1987), incorporated herein by reference as if set forth in its entirety. See also Hu Y., et al., "Monkey organ-cultured anterior segments: technique and response to H-7," Exp. Eye Res. (Jan. 26, 2006) [Epub ahead of print], incorporated herein by reference as if set forth in its entirety.

Baseline IOP is determined in the anterior chambers by administering a control solution (DMEM) to the chambers for twenty-four to seventy-two hours. An ILK inhibitor (e.g., QLT0267) or an agent that interrupts ILK signaling is then administered at a concentration of between about 1 µM and about 100 µM for three hours in one eye of the pair. A decrease in IOP is observed in the treated eye, relative to the control eye.

Prophetic example: A baseline IOP (or baseline outflow facility) is determined in a non-human animal such as a male or female adolescent or young adult Cynomolgus (*Macaca fascicularis*) or rhesus (*Macaca mulatta*) monkey for forty-five minutes. Using a conventional apparatus and conventional delivery methods, an agent that interrupts ILK signaling is administered to an eye of the animal for a time and in an amount sufficient to reduce the IOP. The agent is suitably introduced into the anterior chamber either topically, by 10 µl bolus injection or 2 ml exchange in the anterior chamber contents. Reservoirs to the eyes are closed for thirty minutes to three hours, then reopened and outflow facility is subsequently measured for forty-five to ninety minutes to provide optimum mixing and maintenance of anterior chamber "drug" levels, while minimizing perfusion-induced resistance washout and degradation of the normal physiology.

Total outflow facility is measured by two-level constant pressure perfusion using Bárány's perfusate. Upon completion of the delivery and measurement regimen, a reduced IOP is observed in a treated eye relative to the pre-treatment pressure and relative to a control, untreated eye.

Prophetic example: An ILK inhibitor or an agent that interrupts ILK signaling is administered to at least one eye of a human subject having abnormally elevated IOP in drops containing the inhibitor at a concentration of between about 1 µM and 1 mM for a time sufficient to increase outflow facility. After treatment, aqueous humor outflow (or IOP) is measured and it is observed that outflow is increased relative to pre-treatment levels and that IOP is lower than before treatment.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set for by the appended claims.

The invention claimed is:

1. A method for reducing intraocular pressure elevation in an eye of a human or non-human mammalian subject having or being susceptible to primary-open-angle-glaucoma-associated elevated intraocular pressure relative to a normal physiological intraocular pressure, the method comprising the steps of:
   administering to the eye an amount of an integrin-linked kinase (ILK) inhibitor selected from the group consisting of KP392 and QLT0267 in an amount sufficient to disrupt actin cytoskeletal organization of trabecular meshwork cells thereby reducing the elevated intraocular pressure; and
   quantifying the reduction in intraocular pressure.

2. A method as claimed in claim 1, further comprising administering an amount of a phosphoinositide-3 kinase (PI3K) inhibitor, wherein the PIK3 inhibitor is LY294000 sufficient to further reduce the intraocular pressure in the ILK inhibitor-treated eye.

* * * * *